United States Patent
Anderson et al.

(10) Patent No.: US 8,784,908 B1
(45) Date of Patent: Jul. 22, 2014

(54) COMPOSITION OF A BONE REPAIR MIXTURE

(71) Applicants: Tracy Scott Anderson, Atlanta, GA (US); Timothy E Taylor, Birmingham, AL (US)

(72) Inventors: Tracy Scott Anderson, Atlanta, GA (US); Timothy E Taylor, Birmingham, AL (US)

(73) Assignee: Vivex Biomedical, Inc., Marietta, GA (US)

( * ) Notice: Subject to any disclaimer, the term of this patent is extended or adjusted under 35 U.S.C. 154(b) by 0 days.

(21) Appl. No.: 13/934,403

(22) Filed: Jul. 3, 2013

(51) Int. Cl.
*A01N 65/00* (2009.01)
*A61K 35/32* (2006.01)

(52) U.S. Cl.
CPC ...................................... *A61K 35/32* (2013.01)

USPC .......................................................... 424/725

(58) Field of Classification Search
None
See application file for complete search history.

(56) References Cited

U.S. PATENT DOCUMENTS

| 7,335,381 | B2 | 2/2008 | Malinin et al. |
| 2012/0141555 | A1 | 6/2012 | Briest |
| 2012/0164225 | A1 | 6/2012 | Cook et al. |
| 2012/0165263 | A1 | 6/2012 | Hiratsuka et al. |
| 2012/0195982 | A1 | 8/2012 | Hu et al. |
| 2012/0301508 | A1 | 11/2012 | Hsieh et al. |

*Primary Examiner* — Michael Meller
(74) *Attorney, Agent, or Firm* — David L King

(57) ABSTRACT

A composition of a bone repair mixture has a quantity of allograft particulate bone having a bone particle distribution of particle sizes less than 700 micron and a quantity of biologic carrier material intermixed with the particulate bone. The biologic carrier material is one of collagen, porous collagen or a collagen mixture. Preferably, the carrier material is exclusively collagen.

7 Claims, 2 Drawing Sheets

COMPOSITION OF A BONE REPAIR MIXTURE

TECHNICAL FIELD

The present invention relates to a composition for bone repair, the composition having a quantity of allograft particulate bone having a particle distribution of less than 700 microns and a biological carrier material intermixed with the bone particle, preferably collagen or a collagen mixture.

BACKGROUND OF THE INVENTION

The use of allograft bone particles to fill defects or cavity repair in bone is well understood in the art. Its use has had varying amounts of success dependent on how the bone particles were cleaned, prepared, processed and sized.

Conventional wisdom believed new bone growth would be facilitated by increasing the surface of the bone. That led to a false belief that bone crushed into a fine powder of less than a micron would be best. In practice, this simply was not the case. The powder when packed into the defect had no void spaces to facilitate new ingrowth.

In U.S. Pat. No. 7,335,381; it was determined that an array of several different particle sizes would help induce new bone growth if the bone was properly cleaned and prepared into particles in a grinding procedure wherein the bone never is heated at or above 40 degrees C. as a result of the grinding.

If the bone was non-demineralized and frozen or freeze dried then the osteoinductive properties would not be degraded and a loss of osteoinductive activity could be avoided.

The result was a superior bone particle mixture. The use of this particle mixture 30 has been successful. Synthetic bone graft material is being used, but these materials simply cannot duplicate the porosity and ability to be resorbable when compared to natural cellular materials.

The application of the bone particle mixture during a bone defect repair is not ideal. Dry application of the bone mixture while not difficult can be messy with some particles spilling out of the defect cavity. Ideally, the bone mixture should be delivered with no spillage and wasted material.

It is an objective of the present invention to provide a non-synthetic bone defect repair composition that accelerates bone growth and can be delivered in a more accurate convenient manner.

SUMMARY OF THE INVENTION

A composition of a bone repair mixture has a quantity of allograft particulate bone having a bone particle distribution of particle sizes less than 700 micron and a quantity of biologic carrier material intermixed with the particulate bone. The biologic carrier material is one of collagen, porous collagen or a collagen mixture. Preferably, the carrier material is exclusively collagen.

The ratio by dry weight of biologic carrier to bone particle is 10% to 50%. The particulate bone particle size distribution has a volumetric void volume of 40% to 60% as measured by placing a predetermined quantity of dry bone particles in a test tube and adding a volume of water or saline solution to the top of the column of bone particles the void volume represented the volume of liquid added. The quantity of biologic carrier is evenly mixed or dispersed with the quantity of bone particles to form the repair mixture. The composition of a bone repair mixture further may have a quantity of saline solution. The composition of bone repair mixture is dispersed and held in saline in a container or a delivery syringe for use in a bone repair procedure. The composition is sterilized.

A prefilled container or syringe has a housing with a delivery nozzle, a plunger and a volume of saline solution. The composition of bone repair mixture is dispersed and held in saline in a container or a delivery syringe for use in a bone repair procedure.

The biologic carrier is provided in a particle size of 10 microns or greater. The biologic carrier is provided in the form of particles, chopped fibers or strands of collagen. The biologic carrier is provided in an average particle size of 150 microns.

DEFINITIONS

As used in this specification, the singular forms "a," "an" and "the" include plural referents unless the context clearly dictates otherwise. Thus, for example, the term "a material" is intended to mean one or more materials, or a combination thereof.

The term "biocompatible" refers to the ability (e.g., of a composition or material) to perform with an appropriate host response in a specific application, or at least to perform without having a toxic or otherwise deleterious effect on a biological system of the host, locally or systemically.

The term "osteoconductive" refers to the ability (e.g., of a composition or material) to passively permit bone growth (e.g., onto and/or into the material). As such, osteoconduction can be characterized as a passive process. A material (e.g., a graft or implant) can be osteoconductive, for example, because it is configured to passively permit growth of bone on a surface of the material. In another example, a material can be osteoconductive because it is configured to passively permit growth of bone into an opening (e.g., a pore) of the material.

The term "osteoinductive" refers to the capability (e.g., of a composition or material) to actively stimulate a biological response which induces bone formation. As such, osteoinduction can be characterized as an active process. Osteoinduction can include the formation and/or stimulation of osteoprogenitor cells, such as osteoprogenitor cells in bodily tissue surrounding or proximate to a graft or implant.

The term "biodegradable" refers to the capability of a material to be degraded, disassembled, and/or digested over time by action of a biological environment (including the action of living organisms, e.g., the patient's body) and/or in response to a change in physiological pH or temperature.

The term "resorbable" refers to the capability of a material to be broken down over a period of time and assimilated into the biological environment.

The phrase "by weight" refers to a weight of components of a composition described herein, such as the weight of the applicable component prior to being added to or mixed with another different component of the composition. For example, the weight can refer to an initial weight of the component measured out before further processing of the component into the bone repair composition.

The term "fibrillar" refers to being in the form of fibrils, and not in the form of fibers. For example, a reference to collagen in the fibrillar form includes collagen fibrils, but not native collagen fibers.

The phrase "non-load bearing application" refers to an application for repair of a void or gap in a bone or another bony structure in which the void or gap to be repaired is not intrinsic to the stability of the bone or bony structure.

BRIEF DESCRIPTION OF THE DRAWINGS

The invention will be described by way of example and with reference to the accompanying drawings in which.

DETAILED DESCRIPTION OF THE INVENTION

Figure 1:
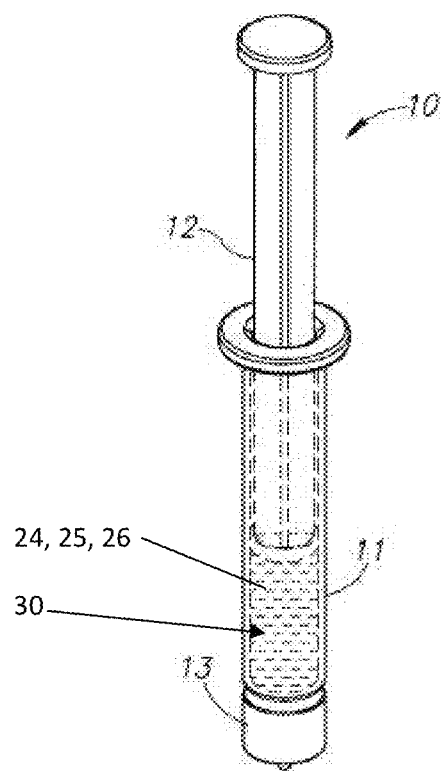
FIG. 1 is a view of a pre-filled syringe with a predetermined amount of the repair mixture in a liquid, preferably saline.
Figure 2:
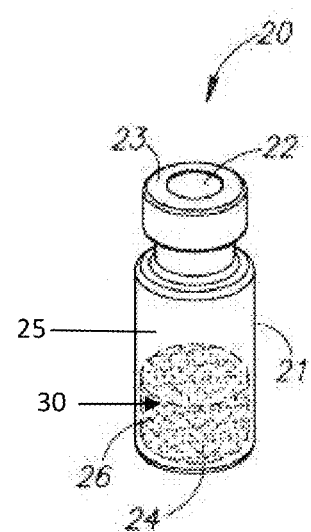
FIG. 2 is a view of a sealed container or vial containing a mixture of bone particles, collagen and saline or other suitable liquid or gel.

As shown in FIGS. 1 and 2, the composition of a bone repair mixture 30 is shown is a pre-filled syringe 10 and a sealed container or vial 20, respectively. The mixture 30 has the bone particles 24 dispersed uniformly in the collagen 26. In either delivery system, the mixture 30 can also be filled with saline or other suitable liquid or gel to facilitate placement in a bone defect or bone cavity prepared for repair.

As shown in FIG. 1, the syringe 10 has a plunger 12 sealed inside the housing 11 closed by a removable cap 13. The plunger 12 withdrawn to provide volumetric space for the pre-filled mixture 30. Once the cap 13 is removed, a nozzle is exposed to deliver the mixture 30 to the target area.

Alternatively, the entire mixture 30 can be provided in a sealed vial or container 20. An end cap 23 encircles an injectable elastomeric stopper at one end or top of a housing 21. The mixture 30 of bone particles 24 and collagen 26 as well as saline 25 or any other suitable fluid or gel is placed inside the container housing.

A composition of a bone repair mixture 30 according to the present invention is configured to facilitate repair or regeneration of bone at a target repair site. For example, in some embodiments, the composition can be osteoconductive, osteoinductive, or both. In all cases, the composition includes a mixture 30 of bone particles 24 and a biological carrier such as collagen 26 or a collagen mixture.

The target repair site can be, for example, a void, gap, or other defect in a bone or other bony structure in a body of a patient. For example, as described in more detail below, the composition can be configured to facilitate bone growth at a target repair site in the spine, pelvis, an extremity, the cranium, or another bone or bony structure in the patient's body. The composition is configured to be disposed at the target repair site. For example, in some embodiments, the composition is configured to be disposed at the target repair site in a non-load bearing application using a delivery device such as a syringe.

The composition can include various combinations of bone particles 24 and collagen 26. The composition is biocompatible and biodegradable. More specifically, the entire composition is preferably resorbable.

The collagen 26 carrier can be or include soluble collagen 26, insoluble collagen 26, or a combination thereof. The collagen 26 can be or include type I collagen 26, type II collagen 26, type III collagen 26, type VII collagen 26, another suitable type of collagen 26, or a combination thereof. For example, in some embodiments, the collagen 26 is or includes medical grade type I collagen 26. In some embodiments, the collagen 26 includes type I collagen 26 and up to about 5% of a type of collagen 26 different than type I collagen 26. For example, the collagen 26 can include type I collagen 26 and up to about 5% type III collagen 26. Specifically, the collagen 26 can include about 5% type III collagen 26 and the remainder of the collagen 26 is type I collagen 26. In another example, the collagen 26 can include type I collagen 26 and up to about 5% type VII collagen 26. The collagen 26 can be human, equine, bovine or porcine. Preferably, the collagen 26 can be derived from human tissue or bone.

In some embodiments, the collagen 26 is in fibrillar form. In some embodiments, at least prior to being implanted into the body of the patient, the collagen 26 is not mineralized. In some embodiments, the collagen 26 is uncompressed.

The collagen 26 of the composition can be a matrix in and/or on which the bone particles 24 are disposed. In this manner, the collagen matrix facilitates delivery of the bone particles 24 to the target repair site. The collagen matrix of the composition can be in any suitable form. For example, in some embodiments, the collagen matrix is in a flowable form. Suitable flowable forms include a slurry, foam, gel, or paste. In this manner, the bone particles 24 can be mixed with and/or embedded into the flowable collagen matrix. In some embodiments, the collagen matrix is a hardened, brittle, or otherwise dry material. For example, the collagen matrix can be formed by drying the flowable collagen 26, as described in more detail below. The dried collagen matrix can be wetted with a suitable solution to form a sponge-like collagen matrix. Suitable solutions include, but are not limited to saline, phosphate buffered saline, gel, or another biocompatible fluid, or any combination of the foregoing. In some embodiments, the collagen 26 can be wetted with a solution that includes at least one of the bioactive glass or calcium phosphate. The collagen matrix, in any suitable form generally and in the dry or sponge-like form particularly, includes a surface configured to receive bone particles 24, for example, in granular or particulate form.

The collagen matrix of the composition is porous. In some embodiments, the collagen matrix defines a plurality of pores. At least a portion of the pores can be configured to permit the in-growth of bone. In this manner, the collagen matrix, and thus the entire composition, is osteoconductive. The porosity of the collagen matrix can be in any suitable range. For example, in some embodiments, the collagen 26 has a porosity or volumetric void volume within the range of about 50% to about 95%. In some embodiments, the bone particles 24 have a porosity or void volume within the range of about 50% to about 90%. More specifically, in some embodiments, the overall bone repair composition is about 25% to 70% porous.

The pores of the collagen matrix can be any suitable size(s) for permitting bone growth therein. For example, in some embodiments, the pores of the collagen matrix each have a nominal or average diameter of 150 microns. The collagen matrix can define pores of various sizes in the range of greater than about 100 microns to less than about 700 microns. In some embodiments, at least a portion of the plurality of pores of the composition are interconnected, which can further facilitate the in-growth of bone. In this way, the bone particles 24 can fill or fit in these pores.

The bone particle composition is configured to facilitate the growth of new bone at the target repair site. The bone is an osteoconductive agent. As described above, the bone can be disposed in or embedded within, and or mixed with the collagen 26. In some embodiments, the bone can be mixed with the collagen 26 such that the bone is randomly, but uniformly dispersed throughout the collagen 26. For example, the bone can be mixed with the collagen 26 to form a substantially homogenous mixture 30 (e.g., a slurry) of collagen 26 and bone.

The bone particles 24 can be in any suitable form. Preferably, the bone is in particulate form. In the particulate form, the bone particles 24 are discrete and generally not interconnected. The bone particles 24 can be generally irregular in shape and can have a smooth or rough surface texture.

The bone particles 24 of the composition accelerate release of BMP and/or other growth factors can be constructed based on a unique particle size distribution of natural bone because the particles 24 have multiple surfaces and are inherently three dimensional. The bone particles 24 have a size of 700 microns or less, the preferred compositions of this invention have a distribution of bone particles 24 all below about 355 microns with at least 30 wt. % of particles 24 having a particle size of less than 180 microns. This particle size distribution provides a unique particulate bone composition of either cancellous bone or cortical bone or mixture 30s thereof with improved osteoinductive activity. This particulate bone can be effectively used as a single preparation or in mixture 30 with various biological carriers such as collagen 26 matrices as described above. The method of bone allograft/xenograft preparation described in the present invention avoids extraction of lipids or inactivation of growth factors and preserves bone composition in its native state.

The present invention is based on the use of Non-demineralized (undecalcified) cortical bone or cancellous bone or mixture 30s thereof in particle sizes less than about 355 microns repeatedly and reliably induces bone formation in defects in bones. Moreover, new bone formation is induced at a rapid rate with direct formation of new osteoid.

The present invention relates to a bone implant composition including a distribution of particles 24 of bone having particle sizes less than or equal to about 355 microns and preferably a mixture 30s of particles 24 having particles 24 sizes between about 355 microns and about 250 microns, particles 24 having particles 24 sizes between about 250 microns and about 150 microns, and particles 24 having particles 24 sizes below about 150 microns, where the compositions have improved osteoinductive activity or osteogenic capacity.

The present invention broadly relates to a method for making a bone implant composition including a distribution of particles 24 of bone having particle sizes of about 355 microns and preferably a mixture 30s of particles 24 having particles 24 sizes between about 355 microns and about 250 microns, particles 24 having particles 24 sizes between about 250 microns and about 150 microns, and particles 24 having particles 24 sizes below about 150 microns, where the compositions have improved osteoinductive activity or capacity, where the method includes the step of periodically grinding a bone sample into a composition of this invention, where the periods between each grinding are sufficient to maintain a temperature of the bone below 40 degrees C., preferably below about 33 degrees C.

The present invention broadly relates to a method for treating bone defects including the step of administering one or more therapeutically effective amount of a bone repair composition including a distribution of particles 24 of bone having particle sizes of about 355 microns to a bone defect, where composition preferably is a mixture 30s of particles 24 having particles 24 sizes between about 355 microns and about 250 microns, particles 24 having particles 24 sizes between about 250 microns and about 150 microns, and particles 24 having particles 24 sizes below about 150 microns, where the compositions have improved osteoinductive activity or capacity.

The present invention also broadly relates to particulate bone composition including a particle size distribution of nascent bone particles 24, autograft bone particles 24, xenograft bone particles 24, allograft bone particles 24 or mixture 30s or combinations thereof with improved osteoinductive capacity.

This micro-particulate bone has superior osteogenic capacity and osteoinductive activity, and in fact, that the smaller the p articles the better the osteoinductive activity. Thus, preferred embodiments of this invention include bone compositions having particle sizes: (a) less than or equal to about 355 microns, (b) less than or equal to 300 microns, (c) less than or equal to 250 microns, (d) less than or equal to 180 microns, (e) less than or equal 106 microns, (f) less than or equal to 75 microns, (g) less than or equal to 53 microns and (h) less than or equal to 25 microns. This composition having smaller particles 24 sizes or particle size distributions including smaller sized particles 24 have superior osteogenic capacity and superior osteoinductive activity.

The osteogenic capacity or osteoinductive activity of the preparations of this invention depend primarily on particle size and retention of unaltered growth factors and other substances. The osteogenic capacity or osteoinductive activity of either cortical bone or cancellous bone or mixture 30s thereof decreases if particles 24 exceed the range of 355 microns. Likewise exposure of the same preparations to hydrogen peroxide, ethyl alcohol or isopropyl alcohol markedly decreases its osteoinductive capacity. The invention is directed to the method of preparation of non-demineralized osteoinductive bone particles 24 as well as to the clinical application of these preparations.

The present invention is directed to implants for stimulating osteoinduction, bone regrowth, and/or bone repair by the implantation of a particulate bone preparation of this invention in a bone defect in an animal including a human. Moreover, the present invention can include particulate bone that has been treated with additional bone growth factors to further enhance and improve bone regeneration after implantation.

The process of particulate bone preparation is equally applicable to allogeneic and xenogeneic bone. The particulate bone preparations of this invention are unique because they avoid entirely the need for harsh chemical treatments and extractions, which alter inherent native properties of bone. The particulate bone preparations of this invention can be produced either from freeze-dried bone not subjected to any chemical treatment or from frozen bone. The invention permits reproducible production of a particulate bone preparation with optimal osteoinductivity clearly demonstrable in higher animal models.

The present invention prepares particulate cortical bone or cancellous bone or mixture 30s thereof without "undesirable constituents." For the purposes of the present invention the term "undesirable constituents" means any constituent other than osteoid tissue normally present in bone or bone marrow. This includes blood, bone marrow, free fat and soft connective tissue elements.

Particulate bone of a powdery consistency can be prepared from previously freeze-dried cortical bone or cancellous bone or mixture 30s thereof. After freeze-drying and associated processing which includes repeated washing in warm saline or other balanced salt solutions to remove "undesirable constituents", the bone is immersed directly into liquid nitrogen vapor and is then freeze-dried in accordance with previously published procedures (Malinin 1, 2, 3) to a residual moisture of 5 to 6% or less. Residual moisture content was determined gravimetrically.

Freeze-dried bone is cut into cubes with a band saw, an oscillating or a rotary saw without heating the bone preparation, by avoiding pressure on the bone being cut and by limiting the time of grinding to no more than 15 second for each surface being cut.

Cut bone cubes, rectangles or other small configurations are further cut in a turbo mill, micro hammer cutter mill, disc mill, toothed disc mill, jet mill or other similar mills capable of grinding bone or reducing bone to particles 24 having a particle size less than about 355 microns. Although usually dry bone is ground, cutting of wet bone preparation can be also accomplished.

Any grinding process is associated with heat production. Heating bone above about 45 degrees C. to about 50 degrees C. is undesirable as the heat significantly reduces to completely abolishes osteoinductive properties of bone. Continuous grinding for 3 to 5 minutes in any of the conventional grinding mills will raise the temperature to 70 degrees C. or above. The preferred method uses defined interrupted grinding so that the temperature exposure to the bone can be carefully controlled and kept below a temperature which would not result in a loss of osteoinductive activity. The mill is operated in cycles of about 8 seconds to about 18 seconds, then the bone is sieved a duration of about 14 seconds to about 15 seconds. This does not allow the temperature of bone or grinder to rise above about 33 degrees C. from the initial temperature of the product of between about 18 degrees C. and about 20 degrees C. The cycle operates for no longer than 3 minutes with an average operating time of about 2.5 minutes.

The above described procedures of repeated grinding and sieving allows for the preparation of specific formulation of non-decalcified particulate bone preparations with high osteoinductive properties. One preferred embodiment of this invention includes compositions having a particle size distributions as follows: (1) from about 24.6 wt % to about 36.3 wt % of particles 24 having a particle size between about 350 microns and about 250 microns; (2) 22 wt % to about 25 wt % of particles 24 having a particle size between 25 microns and about 150 microns; and (3) from about 36.7 wt % to about 46.7 wt % of particles 24 having a particle size less than 150 microns. Particularly, the particles 24 having a particle size below about 25 microns should have the following distribution: 35-65 wt % of particles 24 having a particle size between about 250 microns and about 150 microns, about 10 wt % to about 40 wt % of particles 24 having a particles 24 size between about 150 microns and about 100 microns, and about 10 wt % to about 40 wt % of particles 24 having a particle size less than about 100 microns. More particularly, the particles 24 having a particle size below about 250 microns should have the following distribution: 40 wt % to about 60 wt % of particles 24 having a particle size between about 250 microns and about 150 microns, about 15 wt % to about 35 wt % of particles 24 having a particles 24 size between about 150 microns and about 100 g, and about 15 wt % to about 35 wt % of particles 24 having a particle size less than about 100 microns. Especially, the particles 24 having a particle size below about 250 microns should have the following distribution: 50 wt % of particles 24 having a particle size between about 250 microns and about 150 microns, about 25 wt % of particles 24 having a particles 24 size between about 150 microns and about 100 microns, and about 25 wt % of particles 24 having a particle size less than about 100 microns.

Incorporation of particulate bone allografts is dependent on the size of the particles 24 in the grafts and the method of its preparation. Freeze-dried, microparticulate cortical bone allografts first provide biomechanical support and most rapid healing of the defect into which they are placed. They incorporate by direct ossification, thus producing rapid new bone formation. Demineralized cortical bone powder allografts stimulate the surrounding bone, but by themselves do not undergo accretion. Healing from the periphery is accomplished via as lower process of endochondral ossification.

The bone particles 24, when prepared as described above, are combined with collagen 26 to form a bone repair mixture 30.

In a similar fashion, the collagen 26 constituent in the repair mixture 30 can be prepared into dry particles using a freeze drying method. The collagen 26 can be prepared using the same variety of sizes in the same proportions as described above for the bone particles 24. The two components of bone 24 and collagen 26 can be blended together to form the repair mixture 30. The "dry weight" proportions of the dry particles can be varied or can be identical. It must be appreciated that the bone particles 24 when freeze dried have a resultant density higher than the freeze dried collagen particles 26. Accordingly, if the same dry weight of each is used, the collagen 26 will have a much higher volume of dry material in the order of 2 to 3 times or more than the bone 24. In some cases, this is believed most desirable. Alternatively, in other applications wherein a higher proportion of bone 24 is preferred, the mixture 30 can be blended using equal volumes of each bone 24 and collagen 26. In these mixtures, the dry weight of the freeze dried collagen 26 is about 33% to 50% the weight of the freeze dried bone 24. Regardless, when blended together a thorough mixing and dispersion is believed essential to insure the best performance in terms of new bone ingrowth in the repair procedure. This dispersion is believed best achieved by having the particles sized about the same regardless of the range of particle sizes used in the components. By way of example, if the percentage of bone particles 350-700 microns is 10%; 250-350 microns is 20%; 150-250 microns is 50% and 80-150 microns is 20%; then the collagen particles should preferably be generally the same so upon mixing the dispersion is the same. This means, by weight the bone particles 24 will be 2 to 3 times heavier than the equal volume and sized, but lighter weight collagen 26. This dry mixture can be packaged and stored sterile and dry until use if so desired. However, it is believed at the point of use, the mixture 30 should preferably be rehydrated in sterile saline or other suitable solution to facilitate filling the bone defect. Once hydrated, an irrigation syringe with a large bore nozzle can be used to draw in the mixture 30 and thereafter inject directly into the target or bone repair cavity. Alternatively, if the surgeon prefers the mixture 30 can be applied dry, however, this is believed less desirable due to spillage and waste of the mixture 30 when dry filling a cavity. Ideally, this rehydration is accomplished in a sterile pre-packaged device well before, preferably at the location where manufactured.

In some embodiments, the method optionally includes weighing out at least one component to be included in the material. For example, a desired dry weight of at least one component (e.g., the bone particles 24) can be weighted out. In another example, in some embodiments, the collagen 26 is in a flowable form (such as a slurry of collagen 26 and water). As such, a desired dry weight of collagen 26 is calculated based on the concentration, e.g., of the slurry, and is weighed out volumetrically. For example, to obtain 2 grams of collagen 26 from a slurry having a concentration of 20 mg of collagen 26 per 1 mL of liquid, a 100 mL collagen 26 slurry is volumetrically weighed out.

The basic elements required for bone formation include a three-dimensional, open-porosity tissue scaffold, cells, and osteoinductive signaling molecules to stimulate cell differentiation, proliferation and matrix formation. Successful bone formation requires that these elements be combined in a well-coordinated spatial and time dependent fashion. The relative contribution of each element may vary, e.g., according to differences in patient age, gender, health, systemic conditions, habits, anatomical location, etc.

Embodiments for improved bone formation and healing include the following: biocompatible, open-porous bone tissues scaffold, enhanced local concentration of soluble bone mineral elements such as calcium and phosphate. Each is subsequently analyzed.

A biocompatible, open-porous bone tissue scaffold restores function and/or regenerates bone by providing a temporary matrix for cell proliferation and extracellular matrix deposition with consequent bone in-growth until new bony tissue is restored and/or regenerated. The matrix may also provide a template for vascularization of this tissue.

The macro and micro-structural properties of the scaffold influence the survival, signaling, growth, propagation, and reorganization of cells. They may also influence cellular gene expression and phenotype preservation. The following properties contribute to scaffold characteristics for bone formation: cell biocompatiability, surface chemistry, biodegradability, porosity, and pore size.

In one embodiment, the composition comprises mineralized collagen 26. Mineralized collagen 26 is collagen matrix with bone particles 24 dispersed in them in particular manner, simulating natural bone structure. Collagen 26 is the main protein of connective tissue in animals and the most abundant protein in mammals. Bone is composed of strong, fibrillar bundles of collagen 26 encased within a hard matrix of a calcium phosphate known as hydroxylapatite. Collagen 26 is also a constituent in cartilage, tendon and other connective tissues.

Due to its high degree of biocompatibility with the human body, collagen 26 has been successfully used in a variety of medical and dental applications for many years with minimal adverse responses. During its manufacture, potentially antigenic portions of the collagen 26 molecule are removed, resulting in a product that is highly biocompatible and well-tolerated by the tissue. Collagen 26 is also chemotactic for fibroblasts and other cells involved in bone tissue repair. Collagen 26 biocompatibility ensures that the products are well integrated in the host tissue without eliciting an immune response.

Collagen 26 used in the injectable composition may be from any source. These include natural sources such as human and mammalian tissues, and synthetic sources manufactured using recombinant technologies. It may be of any type (e.g., collagen 26 Types I, II, III, X and/or gelatin). In one embodiment, collagen 26 used is Type I collagen 26. In one embodiment, collagen 26 is derived from bovine dermis. In one embodiment, fibrillar collagen 26 is derived from bovine dermis manufactured by Kensey Nash Corporation (Exton Pa.) under the name Semed F. In one embodiment, the particles 24 comprise at least about 33 percent by dry weight collagen 26. In another embodiment, the particles 24 comprise from about 25 percent to about 75 percent dry weight collagen 26.

The surface chemistry of the scaffold can control and affect cellular adhesion. It can also influence the solubility and availability of proteins essential for intracellular signaling. Intracellular signaling maximizes osteoinductivity through controlled cellular differentiation, proliferation, and stimulation.

Collagen 26 fabricates the disclosed structural scaffold and provides a physical and chemical milieu favorable to bone regeneration. Collagen 26 also provides a favorable extracellular matrix for bone forming cells, e.g., osteoblasts, osteoclasts, osteocytes, etc. The bone forming cells' natural affinity for the collagen matrix has been demonstrated to favorably influence the function and signaling required for normal cellular activity.

The degradation rate of the scaffold should ideally match the bone-healing rate. Slower degradation rates can hinder the rate of remodeled, load-bearing bone formation. Faster degradation can result in unhealed defects.

The solubility and resorption of collagen 26 is affected by its conformation and the degree of collagen 26 cross-linking. The in vivo solubility and resorption of collagen 26 is also influenced by the local concentration of proteolytic agents and vascularity at the site.

Scaffolds desirably possess an open pore, fully interconnected geometry to allow homogeneous and rapid cell in-growth, and facilitate vascularization of the construct from the surrounding tissue.

To this end, the total pore volume porosity of the scaffold simulates that of cancellous bone. Cancellous bone is a highly porous structure (about 50 vol. % to about 90 vol. %) arranged in a sponge-like form, with a honeycomb of branching bars, plates, and rods of various sizes called trabeculae. The synthetic scaffold must ensure pore interconnectivity to allow for the diffusion of nutrients and gases and for the removal of metabolic waste resulting from the activity of the cells within the scaffold. It is generally accepted by one skilled in the art that the pore diameters should be within the range of about 200 microns to about 900 microns range for ideal bone formation. Smaller pores can occlude and restrict cellular penetration, matrix production, and tissue vascularization. Larger pores can detrimentally influence the mechanical properties of the structural scaffold.

The disclosed method produces a composition that mimics the natural structural design of bone for bone formation. In one embodiment, the composition is fabricated using mineralized collagen 26. Mineralized collagen 26 resembles the fundamental element of natural bone, allows the formation of a composition with high surface area and an interconnected network of high porosity.

The disclosed composition and method supplements the local availability of essential soluble bone components, e.g., calcium and phosphate. Biologically compatible, sparingly soluble calcium phosphates are suitable supplements to locally increase the supply of soluble calcium $[Ca^{2+}]$ and phosphate $[PO_4^{3-}]$ ions.

Bone growth factor cytokines, also known as bone morphogenetic proteins (BMPs), are entrapped at high concentration within bone and are secreted by many bone-forming cell types. The primary function of BMPs is cellular signaling. Intracellular signaling occurs through the binding of a soluble growth factor to a specific cell receptor site. This signal pathway stimulates several different and important bone healing events, including the proliferation, migration, and differentiation of bone forming cells. The cells are, in turn, responsible for the synthesis of other proteins and growth factors that are important for regulating and controlling bone tissue formation. Although there is a vast array of BMPs described and known to one skilled in the art, BMPs 2, 4, 6 and 7 are generally considered to be the most osteoinductive.

In one embodiment, the composition forms an injectable fluid paste that enhances the formation of bone tissue. It is provided at a surgical site during reconstruction of a skeletal defect. For example, the injectable composition may be used in spine, dental, reconstructive, trauma, and other orthopedic surgeries. The injectable composition may be used as a substitute for or additive to autologous bone grafts. Although the composition is synthetic, it may include natural components, e.g., bovine collagen 26, and/or be combined with natural components, e.g., bone marrow aspirate.

In one embodiment, the injectable composition is both osteoinductive, i.e., it initiates or induces bone growth, and osteoconductive, i.e., it facilitates already initiated bone growth but does not itself initiate bone growth. Its osteoinductive effect arises, for example, from osteoinductive factors present in the liquid, e.g., bone marrow aspirate, used to make the paste.

In another embodiment, a method of using mineralized collagen 26 and bone particles 24 is disclosed. The particulate composition can be combined with a fluid, for example, water, to create an injectable composition. The composition is then injected, manually applied, or otherwise delivered to a site of a bone. In one embodiment, the paste is an injectable bone void filler. The composition provides improved handling and delivery capabilities, allowing a surgeon to introduce the composition into complex geometry bone defects. The composition components are fully resorbable and stimulate bone regeneration in a manner similar to that achieved with natural bone.

In one embodiment, the composition contains particulate, mineralized collagen 26 and bone particles 24. The composition can be combined with a liquid such as biological fluids (e.g., bone marrow aspirate, whole blood, serum, plasma, etc.) to form an injectable paste. The paste is then used as an injectable and/or conformable (i.e., moldable) bone-grafting material for primary applications in, e.g., spine fusion, dental furcation augmentation, fracture repair, etc.

In one embodiment, where a collagen 26 component is combined with a bone particle component to produce a mineralized collagen 26 component, porous particles 24 of the mineralized collagen 26 component may be prepared. In one embodiment, the mineralized collagen 26 mixed with calcium sulfate in a ratio from about 0.5% to 50%. In another embodiment, the mineralized collagen 26 mixed with bone in a ratio from 5-30%.

In one embodiment, where a collagen 26 component is combined with a bone particle component to produce a mineralized collagen 26 component, porous particles 24 of the mineralized collagen 26 component may be prepared.

The composition may further comprise additives such as bioactive agents, e.g., agents that exhibit biologic activity, and liquids. For example, agents that are osteoinductive and/or osteogenic may be included. As previously stated, osteoinductive agents stimulate bone growth. Examples of osteoinductive agents include bone growth factors, bone marrow components, blood components, and bone components. Bone growth factors may be purified or recombinant and include bone morphogenetic protein (BMP). Bone marrow aspirates (BMA) may be used in the composition because they contain osteoinductive agents such as bone growth factors and mesenchymal stem cells. Mesenchymal stem cells (MSCs) are multi-potent cells capable of differentiating along several lineage pathways to aid in the production of bone. MSCs are considered as a readily available source of cells for many tissue engineering and regenerative medicine applications. For these reasons, osteoinductive proteins and MSCs have been used to supplement the performance of osteoconductive bone formation scaffolds as replacements for autologous and allogeneic bone grafts.

Adding liquid to the composition results in an injectable composition, defined as soft masses with physical consistencies between a liquid and a solid. The liquid may be a biological fluid such as blood, plasma, serum, bone marrow, etc., or may be a buffer or may be capable of buffering to the physiological pH values of human serum (pH 7.1 to pH 7.4). Examples of buffers are known to one skilled in the art and include Tris and phosphate-buffered saline. In one embodiment, the composition has a pH in the range of about pH 5 to about pH 7.4. In another embodiment, the composition has a pH in the range of about pH 5.5 to about pH 6.9. More than one liquid may be included in the composition. For example, the composition may include bone marrow aspirate and a buffering salt solution. The liquid may also include biocompatible liquids such as water, saline, glycerin, surfactants, carboxylic acids, dimethylsulfoxide, and/or tetrahydrofuran. In one embodiment, the liquid is greater than about 25 percent by volume of the composition. In another embodiment, the liquid comprises from about 30 percent to about 55 percent by volume of the composition. Additionally, natural and synthetic polymers such aliphatic polyesters, polyethylene glycols, polyanhydrides, dextran polymers, derivatized above mentioned polymers, and/or polymeric orthophosphates may be included in the composition.

In one embodiment, a process for producing a particulate mineralized collagen 26 composition comprising collagen 26 and calcium sulfate is provided. In one embodiment, a mineralized collagen 26 and calcium sulfate composition is prepared and is then formed into particles 24, as shown in FIG. 3. The types of collagen 26 that may be used are described above and include bovine dermal collagen 26. Suitable calcium phosphate includes acidic calcium phosphate such as monocalcium phosphate [$Ca(H_2PO_4)_2$], calcium hydrogen phosphate [$CaHPO_4$], and/or calcium pyrophosphate [$2CaO \cdot P_2O_5$]. Mineralized collagen 26 then can be further processed by freezing, lyophilization, and the solid composition is formed into particles 24. Methods of forming particles 24 are known to one skilled in the art and include, but are not limited to, grinding, milling, chopping, and/or molding. In one embodiment, particles 24 are formed by milling the solid composition. Milling may occur using a Wiley mill (Thomas Scientific, Swedesboro N.J.). The mesh size on the mill directs the size of the resultant particles 24. In one embodiment, a −20 mesh is used that creates particles 24 in the range of about 100 microns to about 840 microns. The particles 24 may be sized by, for example, sieving. At any point in the process, additional components may be added to the composition, as described above. For example, an osteoinductive component can be added prior to forming the articles.

Upon combining the mineralized collagen 26 with bone particles 24, the composition may be provided as a kit. In one embodiment, the kit includes the composition described above, and may further include other components. These include a receptacle such as a plastic container in which to place the composition and in which to add liquid to form the composition into a paste or putty, a mixing implement such as a spatula, stir rod, etc., a disposable syringe barrel without a needle in which to place and deliver the mixed paste, instructions for formulating and/or using the composition, etc.

In another embodiment, a method of facilitating bone growth is provided. In one embodiment, the method includes adding at least one osteoinductive component such as a purified bone growth factor, a recombinant bone growth factor, a bone marrow component, a blood component, demineralized bone, autologous bone, etc., to the particulate composition previously described. In embodiments where the osteoinductive component is bone marrow aspirate, blood, or a blood component, it may be acutely obtained and added to the composition (e.g., blood and/or bone marrow may be obtained from the same surgical site for repairing the defect). Adding the osteoinductive component(s) and/or another liquid to the composition, with stifling, results in a paste or putty, which is provided to the desired anatomical site of the patient.

In one embodiment, the paste is loaded into the barrel of a disposable 5 cc syringe, without a needle attached, and is extruded through the barrel aperture to the desired anatomical site. In another embodiment, the putty is manipulated or formed into a configuration of desired size, shape, length, etc., either manually or by instrumentation, and gently pressed on and/or in the desired anatomical site. The site is desirably prepared to expose healthy bleeding bone, facilitating subsequent bone growth. The method may be performed using minimally invasive procedures known to one skilled in the art. The method may be used in at least partially filling bone voids and/or gaps of the skeletal system (i.e., extremities, pelvis, spine, oral cavity) that are not intrinsic to the stability of the bone structure. These voids and/or gaps may be a result of trauma, either natural or by surgical creation. The paste is gently provided on and/or in the void and/or gap. The paste is resorbed by the body during the healing process (over days, weeks, and months). The paste may be molded into the bone void or defect by manipulating either manually or using an instrument (e.g., spatula, syringe, probe, cannula, etc.).

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. A prefilled container with a delivery nozzle or a syringe with a delivery nozzle for bone repair consisting essentially of a therapeutically effective amount of allograft particulate bone having a bone particle distribution of particle sizes less than 700 micron and a therapeutically effective amount of collagen.

2. The prefilled container with a delivery nozzle or a syringe with a delivery nozzle of claim 1 wherein the ratio by dry weight of collagen to allograft particulate bone is 10% to 50%.

3. The prefilled container with a delivery nozzle or the syringe with a delivery nozzle of claim 1 wherein the prefilled container with a delivery nozzle or the syringe with a delivery nozzle is sterilized.

4. The prefilled container with a delivery nozzle or the syringe with a delivery nozzle of claim 1 wherein the collagen is provided in a particle size of 10 microns or greater.

5. The prefilled container with a delivery nozzle or the syringe with a delivery nozzle of claim 1 wherein the collagen is provided in the form of chopped fibers of collagen or strands of collagen.

6. The prefilled container with a delivery nozzle or the syringe with a delivery nozzle of claim 1 wherein the collagen is provided in an average particle size of 150 microns.

7. A prefilled container with a delivery nozzle or a syringe with a delivery nozzle for bone repair consisting essentially of a therapeutically effective amount of allograft particulate bone having a bone particle distribution of particle sizes less than 700 micron, a therapeutically effective amount of saline, and a therapeutically effective amount of collagen.

* * * * *